United States Patent [19]

Evans et al.

[11] 4,113,738
[45] Sep. 12, 1978

[54] CONVERSION OF N-TOSYLSULFOXIMIDES TO SULFOXIMINES

[75] Inventors: David H. Evans; Richard B. Greenwald, both of Cambridge, Mass.

[73] Assignee: Polaroid Corporation, Cambridge, Mass.

[21] Appl. No.: 784,669

[22] Filed: Apr. 5, 1977

Related U.S. Application Data

[63] Continuation-in-part of Ser. No. 764,862, Feb. 2, 1977, abandoned, which is a continuation-in-part of Ser. No. 679,487, Apr. 23, 1976, abandoned, which is a continuation-in-part of Ser. No. 591,463, Jun. 30, 1975, abandoned.

[51] Int. Cl.$^2$ .................................... C07D 339/08
[52] U.S. Cl. .......................... 260/327 M; 260/551 S
[58] Field of Search ...................... 260/327 M, 551 S

[56] References Cited

U.S. PATENT DOCUMENTS

| | | | |
|---|---|---|---|
| 2,648,705 | 8/1953 | Reiner | 260/534 |
| 3,255,116 | 6/1966 | Berry | 252/95 |
| 3,376,338 | 4/1968 | Anderson | 260/551 |
| 3,557,206 | 1/1971 | Lyness | 260/551 |
| 3,637,664 | 1/1972 | Satzinger | 260/239 |
| 3,654,359 | 4/1972 | Grosselink | 260/551 S |
| 3,868,418 | 2/1975 | Herrmann | 260/558 S |
| 3,919,310 | 11/1975 | Herrmann | 260/551 S |

*Primary Examiner*—Cecilia M. Jaisle

*Attorney, Agent, or Firm*—Sybil A. Campbell

[57] ABSTRACT

This application is directed to a novel cleavage reaction whereby N-tosylsulfoximides of the following formula are converted to the corresponding sulfoximines. The relevant sulfoximides are represented by the formula:

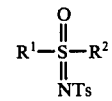

wherein $R^1$ and $R^2$ when taken individually (1) each represent an alkyl moiety containing up to 20 carbon atoms, unsubstituted with an alkali-stable group or (2) $R^1$ is an alkyl moiety containing up to 20 carbon atoms and $R^2$ is $-(CH_2)_n-S-R^3$ wherein $n$ is greater than or equal to 2 and $R^3$ is an alkyl moiety containing up to 20 carbon atoms and $R^1$ and $R^2$ when taken together represents (a) an alkylene moiety having 5 or 6 carbon atoms unsubstituted or substituted with an alkali-stable group; (b) $+CH_2+_xSO_2+CH_2+$ wherein $x$ is 3 or 4; or (c) $+CHR+SO_2+CH_2CR'R''CH_2+$ where R is hydrogen, or thioether R' and R'' when taken individually are hydrogen or alkyl and R' and R'' when taken together is a spiro group, preferably 1,3-dioxolane-2.

This cleavage is accomplished by the use of ammonia and an alkali metal under defined reaction conditions which method affords a higher yield of sulfoximine and a product which is thereby more readily isolated and purified.

18 Claims, No Drawings

0
CONVERSION OF N-TOSYLSULFOXIMIDES TO SULFOXIMINES

CROSS-REFERENCE TO RELATED APPLICATIONS

This application is in part a continuation of copending application Ser. No. 764,862, now abandoned filed Feb. 2, 1977 which is a continuation-in-part of copending application Ser. No. 679,487, filed Apr. 23, 1976, now abandoned which is a continuation-in-part of copending application Ser. No. 591,463, filed June 30, 1975, now abandoned.

BACKGROUND OF THE INVENTION

This invention relates to a novel cleavage reaction for conversion of a defined class of alicyclic N-tosylsulfoximides, the thioether-substituted derivatives of these compounds and certain aliphatic N-tosylsulfoximides, to the corresponding sulfoximines, which specific method of cleavage results in improved yields of these compounds and more facile isolation of the same.

DESCRIPTION OF THE PRIOR ART

The first synthetic example of a sulfoximine was prepared in 30% by weight yield by Whitehead and Bentley, J. Chem. Soc., 1950, p. 2081, by cleavage of the corresponding N-tosylsulfoximide with concentrated sulfuric acid. This method is still employed where it is not desirable to obtain sulfoximines directly by reaction of the appropriate sulfoxides with hydrazoic acid; see for example, C. R. Johnson and C. W. Schroeck, J. Amer. Chem. Soc., 90, 6852 (1968) and D. J. Cram et al., ibid., 92, 7369 (1970). The application of sulfuric acid hydrolysis to N-tosylsulfoximides by Greenwald et al, Tetrahedron Letters 1975, 3885 led to the isolation of the corresponding sulfoximine in 20% to 30% yield with considerable difficulty encountered in its isolation and purification.

The subject invention is concerned with the cleavage reaction on the oxidation products of aliphatic and alicyclic mono-N-tosylsulfimides and certain thioether-substituted derivatives of some of these compounds such that the yield of the corresponding sulfoximines is appreciably increased over prior art yields while the difficulties previously encountered with the isolation and purification of these sulfoximines are diminished.

SUMMARY OF THE INVENTION

It is therefore the primary object of the present invention to provide a novel method of cleaving the N-tosyl moiety from a defined class of aliphatic and alicyclic N-tosylsulfoximides and thioether-substituted compounds of the latter to derive the corresponding sulfoximines or alicyclic thioether-substituted sulfoximines respectively.

It is yet another object of the immediate invention to provide a method of performing said cleavage reaction whereby the yields of the respective sulfoximines and thioether compounds are appreciably increased.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

According to the present invention, it has been found that certain aliphatic and alicyclic N-tosylsulfoximides as well as the thioether-substituted derivatives of the latter when cleaved by the use of liquid ammonia and metallic sodium provide a significantly increased yield of the corresponding sulfoximines of these compounds over prior art methods while at the same time facilitating the isolation and purification of these end products. As mentioned earlier, cleavage of an N-tosylsulfoximide to derive the corresponding sulfiximines has, in the past, been carried out by the use of concentrated sulfuric acid. While this method is still employed in some instances, only a 20% to 30% yield of the sufoximine is obtained as compared to the 50% and as high as 85% yields achieved by the novel method of this invention.

As illustrated by (1) in the following reaction sequence, the reaction of an aliphatic or alicyclic N-tosylsulfoximide or the alicyclic thioether-substituted derivatives thereof with liquid ammonia and metallic sodium will effect the cleavage reaction to give the corresponding sulfoximine (2):

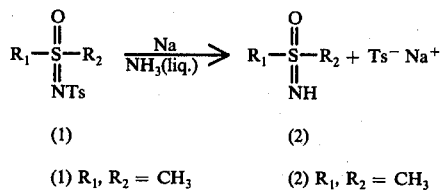

For example, dimethyl-N-tosylsulfoximide is converted to dimethylsulfoximine by first combining the former with an amount of liquid ammonia such that a workable suspension is obtained. Metallic sodium spheres are then added to the suspension in an amount which is in excess of the amount of dimethyl-N-tosylsulfoximide present; usually at least about 3 equivalents of sodium per equivalent of sulfoximide. When the addition is complete, the reaction mixture is allowed to stir at refluxing ammonia temperature, approximately − 30° C, and below.

The sulfoximines produced by the cleavage reaction of the present invention are represented by the formula:

wherein $R^1$ and $R^2$ when taken individually (1) each represent an alkyl moiety containing up to 20 carbon atoms, preferably a lower alkyl containing 1 to 4 carbon atoms, unsubstituted or substituted with an alkali-stable group or (2) $R^1$ is an alkyl moiety containing up to 20 carbon atoms, preferably a lower alkyl containing 1 to 4 carbon atoms and $R^2$ is $(CH_2)_nS-R^3$ wherein n is an integer greater than or equal to 2 and $R^3$ is an alkyl moiety containing up to 20 carbon atoms, preferably a lower alkyl having 1 to 4 carbon atoms and $R^1$ and $R^2$ taken together represent (a) an alkylene having 5 to 6 carbon atoms unsubstituted or substituted with an alkali-stable group, preferably unsubstituted; (b) $\{CH_2\}_xSO_2\{CH_2\}$ wherein $x$ is 3 or 4, preferably 3; or (c) $\{CHR\}SO_2\{CH_2CR'R''CH_2\}$ where R is hydrogen, thioether, preferably alkylthioether, R' and R'' taken individually are hydrogen or alkyl and when R' and R'' are taken together is a spiro group, preferably 1,3-dioxolane-2. Moieties containing substituents that may be incompatible with the conditions of the cleavage reaction such as but not limited to $-NO_2$, $-CN$, $-X$ where X is halogen etc. may be introduced into the parent system following the cleavage reaction of the present invention either by alpha-alkylation on carbon following methods described herein or by alkylation on nitrogen as described in part in U.S. patent application Ser. No. 764,864.

In preparing these compounds according to the method of this invention it is necessary to cleave the corresponding N-tosylsulfoximide of the formula:

(II)

wherein $R^1$ and $R^2$ are as defined above and Ts represents

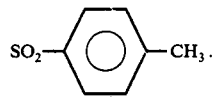

These N-tosylsulfoximide starting materials are derived from the corresponding aliphatic sulfides or the alicyclic sulfides, i.e., thiane, m-dithiane and thiolane, thiepane, and m-dithiepane. The alicyclic N-tosylsulfoximide starting materials may be prepared according to the procedures described in the aforementioned application Ser. No. 764,862, which for convenience, is incorporated herein by reference.

Accordingly, the alicyclic sulfides are reacted with an aromatic N-chlorosulfonamide such as N-chloro-p-toluene sulfonamide sodium salt (hereinafter referred to as Chloramine-T) or N-chloro-benzenesulfonamide sodium salt (hereinafter referred to as Chloramine B) in aqueous alkanol solution at a temperature between about 20° C and 30° C to yield the corresponding mono-N-tosylsulfimide. In this reaction, the solution generally is an aqueous solution of a lower alkanol having 1 to 4 carbon atoms, e.g., methanol or ethanol and contains between about 75% to about 95% by weight of the alkanol. At least one molar equivalent and usually between about one to two molar equivalents of The aromatic N-chlorosulfonamide sodium salt are reacted with one equivalent of the above-described sulfides.

The unfunctionalized sulfur in the case of m-dithianes is then selectively oxidized by reacting one molar equivalent of the mono-N-tosylsulfimide with two to four molar equivalents of 40% by weight peracetic acid in glacial acetic acid at about 20° C to 30° C to yield the corresponding β-sulfonyl N-tosylsulfimide.

Further oxidation of the above system to convert the β-sulfonyl N-tosylsulfimides to the corresponding sulfoximides may be carried out by reacting one molar equivalent of the sulfimide compound with at least about one molar equivalent of potassium permanganate in acetic acid-acetic anhydride solution at about 20° to 30° C.

The sulfonyl N-tosylsulfoximides may in turn be synthesized directly from the sulfide/mono-N-tosylsulfimides by reacting one molar equivalent of the latter with at least 3, preferably about 6 to 7, molar equivalents of potassium permanganate in acetic acid - acetic anhydride solution at about 20° C to 30° C.

The open-chain N-tosylsulfoximides are synthesized as in the case of the alicyclic sulfoximides from the N-tosylsulfimides. These in turn are derived from sulfides of the formula:

(III) $R^4-S-R^5$ where $R^4$ and $R^5$ are (1) alkyl moieties containing up to 20 carbon atoms, the same or different, or (2) $R^4$ is alkyl containing up to 20 carbon atoms and $R^5$ is $\{CH_2\}_mS-R^6$ were $m$ is greater than or equal to 2 and $R^6$ is alkyl, preferably a lower alkyl containing 1 to 4 carbon atoms. It will be understood that when a compound wherein $R^5$ as defined by (2) is subjected to the conditions of the above-described Chloramine-T oxidation, a di-N-tosylimino product may be obtained which in turn as the corresponding disulfoximino derivative would be subject to the cleavage conditions herein described. As in the case of the alicyclic sulfoximines discussed previously, all moieties containing substituents other than those which are compatible with the conditions of the cleavage reaction, for example, ketal, acetal, carboxyl, sulfonyl groups and simple alkyl ethers should be introduced by the appropriate method, e.g., alkylation of the sulfoximine subsequent to the cleavage reaction of this invention. The aliphatic sulfides are treated with an aromatic N-chlorosulfonamide, preferably Chloramine-T, under the same experimental conditions as discussed previously to yield the corresponding aliphatic mono-N-tosylsulfimide of formula:

(IV)

where $R^4$ and $R^5$ have the same meaning as ascribed in formula III and Ts represents

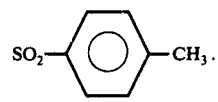

these aliphatic sulfimides are in turn oxidized as, for example, by the method discussed in relation to the alicyclic sulfimides to yield the corresponding N-tosylsulfoximides of the formula:

(V)

wherein $R^4$, $R^5$ and Ts have the same meaning as assigned in formula IV.

The thioether-substituted sulfoximines may be synthesized via two avenues of preparation, both of which are two-step processes and both of which preparations employ the cleavage reaction of the present invention to derive the sulfoximine.

The first method of synthesis is to initially alkylate the N-tosylsulfoximide with the thioether alkylating agent, for example, R⁰S(CH₂)ᵧ-Z where R⁰ is an aliphatic hydrocarbon radical, preferably alkyl, Z is, for example, tosyl or mesyl when y is 0; or, for example, chloro when y is a positive integer greater than 1, to derive the thioether-substituted N-tosylsulfoximide. This product in turn cleaved by the method of this invention to derive the thioether-substituted sulfoximine. Other substituents, particularly those containing non-alkali-stable groups desired to be present in the sulfoximine molecule, may be added at this time. The same improved yield is obtained for these thioether substituted sulfoximines as that evidenced with the unsubstituted sulfoximines.

Secondly, the N-tosylsulfoximide may first be cleaved according to the parameters set forth in this disclosure to give the respective sulfoximine which is in turn alpha-alkylated with, for example, R⁰S(CH₂)ᵧZ where R⁰, Z and y are as defined above to yield the corresponding thioether-substituted sulfoximine.

Examples of organic compounds containing the moiety

wherein Ts represents

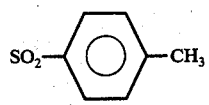

and on which compounds the cleavage reaction of the present invention may be performed include, but are not limited to:

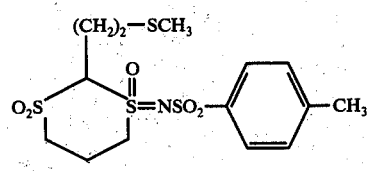 (1)

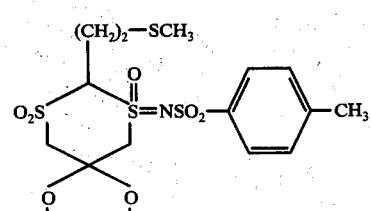 (2)

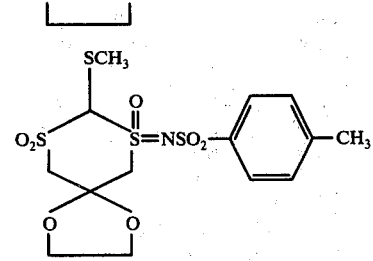 (3)

-continued

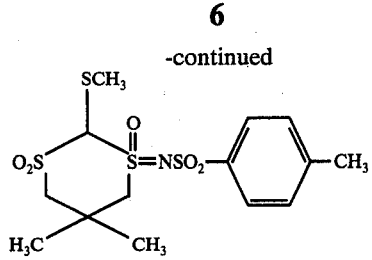 (4)

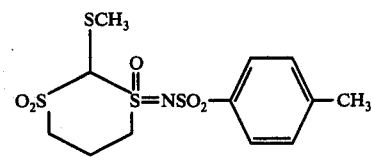 (5)

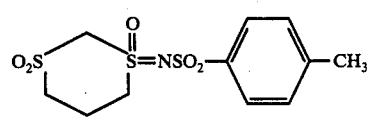 (6)

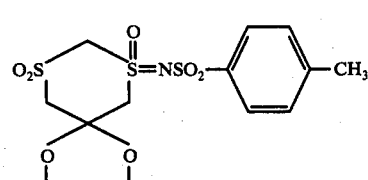 (7)

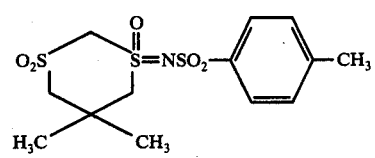 (8)

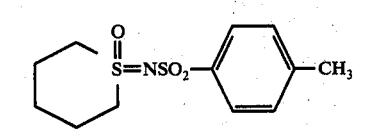 (9)

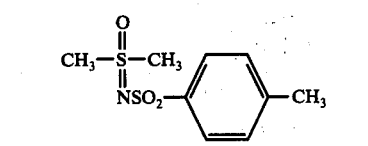 (10)

Whether one chooses to perform the cleavage reaction of the present invention on the thioether-unsubstituted N-tosylsulfoximide starting materials or on their thioether-substituted derivatives, the parameters of this inventive reaction are the same, namely, treatment of the N-tosylsulfoximide starting material with alkali metal in liquid ammonia under the following prescribed condition.

In this method although the presence of, e.g., sodium and ammonia are essential, the ratio of one to the other is not critical. The one proviso is that there be a sufficient amount of the ammonia solvent present to obtain a workable suspension of the reactants. Once the suspension is obtained, the metallic spheres are added. It is important, however, that an excess of the metal be used in relation to the amount of N-tosylsulfoximide present. It has been established that not less than about 3 equivalents of the metal per equivalent of N-tosylsulfoximide should be present; 4 or 5 equivalents of metal being generally employed with greater than 5 equivalents being operative but unnecessary.

Once the reactants are in suspension the cleavage reaction is conducted at refluxing ammonia termperatures, i.e., at about −30° C, or below.

The following examples are given to further illustrate the present invention and are not intended to limit the scope thereof:

EXAMPLE I

Preparation of:

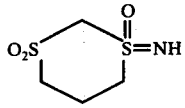

(1) 1-Tosylimino-1,3-dithiane: A suspension of 1,3-dithiane (20 g., 166 mmols) in 150 ml of pyridine was treated with Chloramine-T trihydrate (104 g., 366 mmols) in portions over 1 hr. The exothermic reaction was moderated with a cold water bath so that the temperature of the reaction remained below 35° C. During the addition period a dark green color developed. The reaction was stirred for 3 hrs. whereupon the green color was dissipated to give a rusty orange suspension. The mixture was poured into 1 liter of cold water. The white solid which separated was collected, washed thoroughly and dried to give 37 g. (77%) of material (melting range 164° C - 165° C).

(2) 1-Tosylimino-1,3-dithiane-1,3,3-trioxide: To a suspension of finely ground potassium permanganate (144 g., 900 mmols) in 500 ml. acetic acid/160 ml. acetic anhydride contained in a 1 liter 3 necked round bottomed flask fitted with mechanical stirrer and thermometer, 1-tosylimino-1, 3-dithiane (40 g., 138 mmols) prepared according to the method of step 1 was added in portions over 2 hours while moderating the reaction mixture with a cold water bath so that the temperature was less than 35° C. The reaction mixture was allowed to reach ambient temperatures slowly in the cooling bath and to stir for 3 days. The insoluble material was collected by suction, pressed dry and suspended in 500 ml. cold water. Saturation with sulfur dioxide (cooling bath temperature less than 20° C) was continued until a light beige suspension prevailed. The solid was collected, washed well with water and air-dried to give 36.3 g. (78% yield) of material having a melting range of 214°-217°. This material was shown to be essentially homogeneous by TLC, containing only traces of immobile impurities. An analytical sample could be obtained by crystallization from 1:1 EtOH/H₂O (1 g./50 ml.). (3) Into a 500 ml. three necked round bottomed flask fitted with a Dry Ice/acetone coldfinger condenser and cooled in a Dry Ice/acetone bath about 160 ml. of ammonia was distilled. 1-Tosylimino-1,3-dithiane-1,3,3-trioxide: (16 g.; 47.5 mmols) obtained in step 2 was added in one portion. To the resulting magnetically stirred suspension, sodium spheres (4.4 g., 190 mmols) were added over 1 hour allowing most of one portion to dissolve before adding the subsequent portion. A transient dark blue color was observed. When the addition was complete, the cooling bath was removed, and the reaction mixture was allowed to reflux under the coldfinger for 3-4 hours. A light tan near-solution resulted. The ammonia was allowed to evaporate slowly overnight (in hood) and the last traces were purged in a nitrogen stream. A brownish solid residue remained which was chilled in an ice bath before adding 100 ml. cold water (initially, dropwise). The resulting suspension was stirred for 0.5 hour and filtered to remove a dark sludge. The light tan filtrate was chilled in an ice bath and neutralized to pH∼6.5 by the dropwise addition of concentrated hydrochloric acid (ca. 6 ml. was required). Unreacted starting material precipitated and was removed by filtration, and the pale amber filtrate was evaporated to dryness on a rotary evaporator (benzene chaser). Extraction for 16 hours of the granular white residue with acentonitrile, cooling the extract to room temperature, removing insoluble material by filtration, and evaporation of solvent in vacuo afforded the title compound (6 g., 85%) as a creamy white powder. An analytical sample was obtained by crystallization from acetonitrile (1 g./35 ml.), m.p. 214-216°.

EXAMPLE II

Preparation of the compound having the formula:

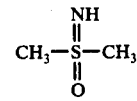

N-Tosyldimethylsulfoximine (10.0 g., 40.5 mmoles) was suspended in about 150 ml. of liquid ammonia to which resultant suspension was added sodium spheres [4.65 g., 202 mmoles] in portions over 0.5 hour. The reaction mixture was stirred for about 2 hours under Dry Ice-/acetone coldfinger and the ammonia was then allowed to evaporate slowly overnight (about 16 hours).

Residual traces of ammonia were removed under nitrogen stream while the off-white powder was simultaneously warmed in a water bath and subsequently chilled in an ice bath. Cold water (50 ml.) was added, initially dropwise, to the mixture and the solution stirred for about 1 hour. The solution was then filtered to remove the insoluble materials and the filtrate adjusted to a pH of about 7 with concentrated hydrochloric acid (about 12 ml.). The filtrate was thereafter chilled and the minute amount of insoluble materials therein removed by filtration. The filtrate was then stripped to dryness on a rotovac, extracted with hot alcohol and the insolubles removed. The extract was stripped to give a pasty white solid which was washed twice with hexane. The solid was triturated with ether and collected to give 3.5 grams (93% yield) of an oily white solid. This solid was taken up in hot chloroform and the insoluble material separated by filtration. The filtrate was dried over magnesium sulfate and stripped to give a syrup which readily crystallized on cooling to give 1.5 g. (40% yield) of the title compound as a hygroscopic white solid.

EXAMPLE III

Preparation of the compound having the formula:

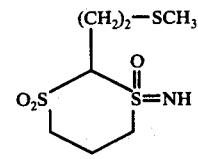

(1) The compound 1-tosylsulfoximino-1,3-dithiane-3,3-dioxide (10 g., 20.5 mmoles) was readily dissolved in dimethylformamide (100 ml.), the solution having been placed in a flamedried 500 ml. three necked round bottomed flask fitted with a thermometer, dropping funnel and a nitrogen inlet. Potassium t-butoxide (3.65 g., 32.5)mmoles was added to the dimethylformamide solution over a 2-minute period. A green color developed which rapidly changed to a dark steel blue.

The suspension was stirred for one hour at ambient temperatures and β-chloroethyl-methyl sulfide (3.6 g., 32.6 mmoles) was thereafter added to the suspension dropwise over a 10-minute period. The blue color was largely dissipated to give a dark tan-colored reaction mixture. The mixture was then stirred for 1.5 hours at ambient temperatures after which the temperature was raised to 70° C. The mixture was maintained at 70° C for approximately 16 hours during which time the color of the reaction mixture lightened and some white solid separated.

On evaluation by thin layer chromatography at this stage of the reaction (using 10% methanol/chloroform on silica gel) only a minor amount of unconverted starting material was found to be present.

The reaction mixture was allowed to cool and was then poured into cool water. The gummy precipitate was extracted with chloroform which extract was thereafter washed thrice with water (200 ml. per washing). The extract was then dried over magnesium sulfate, stripped and triturated with several portions of ether to give a solid residue (9.4 g.) which was taken up in boiling ethanol-2B (100 ml.) in which the residue was not entirely soluble to give a white granular solid. This was allowed to stand for about 72 hours. The solid was collected to give 7.3 g. of the compound (melting range 112° C – 118° C) having the formula:

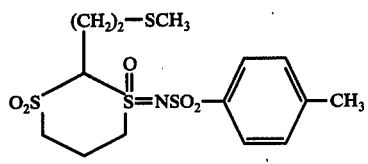

(2) The compound obtained in step 1 (1.5 g., 3.54 mmoles) was added to liquid ammonia (30 ml.) in a three neck flask fitted with a Dry-Ice condenser and a drying tube. A very pale yellow partial solution resulted. Sodium(spheres) (0.35 g., 14.6 mmoles) was added to the solution in portions over a 20-minute period. A transient green-blue color formed near the dissolving sodium. When the addition of the sodium spheres was complete, a lemon yellow suspension resulted.

The yellow suspension was maintained at a slow reflux for about 2 hours and was then allowed to evaporate over a 16-hour period. It was noted that after about 30 minutes of reflux time the yellow color was almost dissipated and disappeared after one hour.

The resultant cream-colored residue was taken up in water (30 ml.) to give a pale yellow solution. The solution was filtered to remove a small amount of flocculant material which solution was then neutralized to a pH of 6–7; about 2 ml. of concentrated hydrochloric acid was required. The pH-adjusted solution was cloudy and remained slightly cloudy after being filtered. The solution was stripped on a rotary evaporator to give a granular white solid.

On examination by TLC using 10% methanol/chloroform on silica gel, no unconverted starting material remained. The crude residue was boiled in acetonitrile and thereafter filtered to remove the insoluble materials. On evaluation by TLC, the remaining composition was largely homogenous. The residue (0.7 g.) was dissolved in hot acetonitrile (about 18 ml.) and allowed to stand. The title compound (0.7 g.) was collected (melting range of 165° C – 167.5° C).

Since certain changes may be made in the above compositions and processes without departing from the scope of the invention herein involved, it is intended that all matter contained in the above description should be interpreted as illustrative and not in a limiting sense.

What is claimed is:

1. A method which comprises reacting about 1 molar equivalent of an N-tosylsulfoximide of the formula:

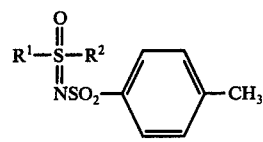

wherein $R^1$ and $R^2$ when taken individually (1) each represent an alkyl moiety containing up to 20 carbon atoms, unsubstituted or substituted with an alkali-stable group, or (2) $R^1$ is an alkyl moiety containing up to 20 carbon atoms and $R^2$ is $(-CH_2)_n-S-R^3$ wherein n is greater than or equal to 2 and $R^3$ is an alkyl moiety containing up to 20 carbon atoms and $R^1$ and $R^2$ when taken together represent (a) an alkylene moiety having 5 or 6 carbon atoms unsubstituted or substituted with an alkali-stable group; (b) $(CH_2)_xSO_2(CH_2)$ wherein x is 3 or 4; or (c) $(CHR)SO_2(CH_2CR'CR''CH_2)$ where R is hydrogen or $R°S(CH_2)_y$ wherein $R°$ is methyl and y is 0 or a positive integer greater than 1, R' and R'' when taken individually are hydrogen or methyl and R' and R'' when taken together are 1,3-dioxolane-2, and at least about 3 equivalents of an alkali metal in liquid ammonia at refluxing ammonia temperatures, to yield the corresponding sulfoximine and isolating said sulfoximine.

2. The method as defined in claim 1 wherein the alkali metal is selected from sodium and potassium.

3. The method as defined in claim 2 wherein the alkali metal is sodium.

4. The method as defined in claim 1 wherein from about 3 to about 5 molar equivalents of the alkali metal are employed per equivalent of N-tosylsulfoximide.

5. The method as defined in claim 1 wherein the reaction is conducted at or below about −30° C.

6. The method as defined in claim 1 wherein $R^1$ and $R^2$ are taken individually and each represents an alkyl moiety containing up to 20 carbon atoms.

7. The method as defined in claim 6 wherein $R^1$ and $R^2$ are both alkyl moieties containing 1 to 4 carbon atoms.

8. The method of claim 7 wherein $R^1$ and $R^2$ are unsubstituted.

9. The method as defined in claim 8 wherein the N-tosylsulfoximide is:

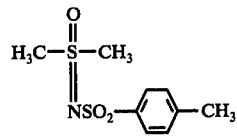

10. The method as defined in claim 1 wherein $R^1$ and $R^2$ are taken together.

11. The method as defined in claim 10 wherein $R^1$ and $R^2$ represent $CH_2)_xSO_2 CH_2$.

12. The method as defined in claim 11 wherein $x$ is 3.

13. The method as defined in claim 10 wherein $R^1$ and $R^2$ represent $(CHR)SO_2(CH_2CR'R''CH_2)$.

14. The method as defined in claim 13 wherein R' and R'' are taken together and are 1,3-dioxolane-2.

15. The method as defined in claim 13 wherein R' and R'' each are hydrogen.

16. The method as defined in claim 13 wherein R' and R'' each are methyl.

17. The method as defined in claim 13 wherein R is hydrogen.

18. The method as defined in claim 13 wherein R is $R°S(CH_2)_y$.

* * * * *